United States Patent
Ahmed et al.

(10) Patent No.: US 11,013,899 B2
(45) Date of Patent: May 25, 2021

(54) MICRONEEDLE PATCHES FOR TRANSDERMAL DELIVERY

(71) Applicant: The Board of Trustees of the Leland Stanford Junior University, Stanford, CA (US)

(72) Inventors: Mohamed R. Ahmed, Stanford, CA (US); Jayakumar Rajadas, Stanford, CA (US); Wenchao Sun, Stanford, CA (US); Mohammed Inayathullah Nazir Ahmed, Stanford, CA (US); Feng Xu, Dallas, TX (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 164 days.

(21) Appl. No.: 15/997,412

(22) Filed: Jun. 4, 2018

(65) Prior Publication Data
US 2018/0344999 A1    Dec. 6, 2018

Related U.S. Application Data

(60) Provisional application No. 62/515,426, filed on Jun. 5, 2017.

(51) Int. Cl.
| | | |
|---|---|---|
| *A61M 37/00* | (2006.01) | |
| *A61B 5/00* | (2006.01) | |
| *A61L 31/12* | (2006.01) | |
| *A45D 40/26* | (2006.01) | |
| *A45D 34/04* | (2006.01) | |
| *A45D 40/00* | (2006.01) | |
| *A45D 34/00* | (2006.01) | |
| *A61B 10/00* | (2006.01) | |
| *A45D 37/00* | (2006.01) | |
| *A61K 9/00* | (2006.01) | |
| *A61M 5/32* | (2006.01) | |
| *A61B 5/01* | (2006.01) | |

(52) U.S. Cl.
CPC ......... *A61M 37/0015* (2013.01); *A45D 34/00* (2013.01); *A45D 34/04* (2013.01); *A45D 37/00* (2013.01); *A45D 40/00* (2013.01); *A45D 40/26* (2013.01); *A61B 5/411* (2013.01); *A61B 10/0035* (2013.01); *A61K 9/0097* (2013.01); *A61L 31/125* (2013.01); *A61M 5/3298* (2013.01); *A45D 2200/00* (2013.01); *A45D 2200/10* (2013.01); *A61B 5/0082* (2013.01); *A61B 5/01* (2013.01); *A61M 2037/0023* (2013.01); *A61M 2037/0046* (2013.01); *A61M 2037/0053* (2013.01); *A61M 2037/0061* (2013.01); *A61M 2205/3306* (2013.01); *A61M 2205/3368* (2013.01); *A61M 2210/0606* (2013.01)

(58) Field of Classification Search
None
See application file for complete search history.

(56) References Cited

U.S. PATENT DOCUMENTS

| | | | |
|---|---|---|---|
| 2005/0013867 A1* | 1/2005 | Lehrman | A61K 9/0075 424/489 |
| 2008/0214952 A1 | 9/2008 | Mir et al. | |
| 2010/0286598 A1* | 11/2010 | Garcia De Castro Andrews | A61M 5/3294 604/60 |
| 2016/0015952 A1* | 1/2016 | Omachi | A61M 37/0015 604/46 |
| 2016/0058377 A1 | 3/2016 | Butte et al. | |
| 2016/0066789 A1* | 3/2016 | Rogers | A61N 1/05 604/20 |
| 2016/0129164 A1 | 5/2016 | Lee et al. | |
| 2017/0080196 A1 | 3/2017 | Lee et al. | |

OTHER PUBLICATIONS

International Search Report and Written Opinion for PCT/US2018/035812 dated Aug. 28, 2018, 8 pages.

\* cited by examiner

*Primary Examiner* — Robert A Wax
*Assistant Examiner* — Randeep Singh
(74) *Attorney, Agent, or Firm* — Sheppard Mullin Richter & Hampton LLP

(57) ABSTRACT

Embodiment provided herein are directed to microneedle patches for agent application on a mammal skin. The microneedle patch may comprise a patch scaffold having a surface, and a plurality of microneedles disposed on the surface. Each of the microneedles may be capable of piercing the skin 50 µm to 1000 µm deep, and comprises a composite material comprising polyvinylpyrrolidone (PVP) and one or more additional copolymers selected from the group consisting of maltose, leucine, and dileucine.

20 Claims, 9 Drawing Sheets

MICRONEEDLE PATCHES FOR TRANSDERMAL DELIVERY

CROSS REFERENCE TO RELATED APPLICATIONS

This application claims the benefit under 35 U.S.C. § 119(e) of U.S. Provisional Application Ser. No. 62/515,426, filed Jun. 5, 2017, the content of which is incorporated by reference in its entirety into the present disclosure.

FIELD OF THE INVENTION

The invention relates generally to transdermal therapies, and more particularly to a microneedle patch for transdermal application of an agent to mammalian skin.

BACKGROUND

Many agents (e.g. cosmetic preparations, chemicals, drugs, vaccines, etc.) may cause mild to severe allergic reactions including contact dermatitis in people. If a person suspects a particular agent is responsible for his/her contact dermatitis, a patch test may be utilized to assess the existence of a contact allergy to said agent. Patch tests are simple in concept, and generally comprise a sheet of material coated with the agent to be tested (e.g., the suspected allergen). The patch is applied to the person's skin to introduce the suspected allergen to the immune system of the patient. After removal of the patch, the presence of an allergic reaction at the application site on the skin may be macroscopically determined. Use of such patch tests, however, is associated with several disadvantages. For instance, the patch test may need to be applied to the person's skin for a long period of time to allow the allergen to diffuse into the skin across the strong, horny exterior thereof (i.e., the stratum corneum). Moreover, there are often issues with accuracy in macroscopically determining the degree to which an allergic response occurs at the application site of the allergen.

Intradermal injection of a suspected allergen via a hypodermic needle is another method commonly used to deliver the antigen to a person's skin. However, use of hypodermic needles is painful and inconvenient for self-administration. Further, the manual insertion of the hypodermic needle may be difficult to control, thus making targeted delivery of the allergen to specific sites within the skin difficult.

Microneedle patches (MNPs) represent a recent, non-invasive transdermal delivery system for suspected allergens. The MNPs typically comprise a pedestal to which microneedles containing an allergen are attached. The microneedles are configured to pierce the skin, and subsequently dissolve upon insertion into the skin for the transdermal delivery of the allergen. Such dissolving microneedles may be less prone to breaking in vivo as compared to conventional silicon and metal needles. Microneedles comprised of polyvinylpyrrolidone (PVP) are often used for the transdermal delivery of allergens.

The current MNPs are also associated with several limitations which hinder their clinical application. For instance, the dissolving microneedles have strict mechanical performance requirements. The microneedles need sufficient mechanical strength to perforate the stratum corneum. Incomplete penetration of needles into the skin leads to an ineffective delivery of the allergen thereto and allergen wastage. Recent studies have shown significant variation in skin penetration across current, dissolving microneedles, which may be fabricated from diverse biomaterials. Pure PVP lacks sufficient biocompatibility, and thus is not an effective biomaterial for use in microneedles. Moreover, the low solubility of PVP also reduces the allergen release rate.

There is therefore a need for an improved device for the transdermal delivery of an agent to mammalian skin, and which overcomes the limitations and disadvantages associated with the use of current patch tests, hypodermic needles, and MNPs.

SUMMARY

The present disclosure provides microneedle patches useful for safe and effective delivery of agent to the skin of a subject. The agent may be a suspected allergen or a pharmaceutically or cosmetically effective agent.

Accordingly, in one embodiment, provided herein is a microneedle patch for agent application on a mammal skin, where the microneedle patch comprises a patch scaffold having a surface, and a plurality of microneedles disposed on the surface. Each of the microneedles is capable of piercing the skin 50 μm to 1000 μm deep and comprises a composite material comprising polyvinylpyrrolidone (PVP) and one or more additional copolymers selected from the group consisting of maltose, leucine, and dileucine.

In some embodiments, each of the microneedles of the microneedle patch further comprises an agent. In some embodiments, each of the microneedles is configured to dissolve and thereby deliver the agent to the mammal upon application on the skin.

In some embodiments, at least two of the microneedles comprise different agents.

In some embodiments, the agent is a cosmetic preparation or a pharmaceutical preparation. In some embodiments, the patch is provided as a facial mask or a portion of the facial mask.

In some embodiments, the agent is uniformly disposed within the composite material of each microneedle.

In some embodiments, each of the microneedles comprises a tip portion proximate a tip of the microneedle and a stem portion that is further distal from the tip. In some embodiments, the agent is not present in the stem portion of each microneedle, or is present at the stem portion at a lower concentration than in the tip portion of each microneedle. In some embodiments, the composite material is present at the tip portion at a lower concentration than in the stem portion.

In some embodiments, each of the microneedles comprises a plurality of layers and each of the layers comprises alternately higher and lower concentrations of the agent.

In some embodiments, the agent is coated on at least a portion of an outer surface of the composite material of each microneedle.

In some embodiments, the microneedle patch further comprises a pedestal on the surface for adhesion to the skin.

In some embodiments, at least one of the one or more additional copolymers of the composite material is maltose. In some embodiments, the one or more additional copolymers of the composite material comprise maltose, leucine, and dileucine.

In some embodiments, the composite material comprises about 70-90 wt. % PVP.

In some embodiments, each of the microneedles comprises a substantially pyramidal shape.

In some embodiments, the microneedle patch further comprises a sensor coupled to the patch scaffold and proximate each of the microneedles. In some embodiments, the sensor is an image sensor or a thermal sensor.

Also provided herein, in one embodiment, is a method for determining an immune response in a mammal skin, where the method comprises: applying a microneedle patch as described herein; and determining, via at least one sensor operatively coupled to the microneedle patch, whether the agent delivered to the mammal from each of the microneedles induces an immune response in the skin thereof. In some embodiments, the sensor utilized in this method comprises an image sensor or a thermal sensor.

Also provided herein, in one embodiment, is a method for delivering a cosmetic or pharmaceutical agent to a mammal skin, the method comprising applying the microneedle patch on the skin and allowing the cosmetic or pharmaceutical agent of the patch to be delivered to the skin.

BRIEF DESCRIPTION OF THE DRAWINGS

Preferred and non-limiting embodiments of the invention may be more readily understood by referring to the accompanying drawings in which.

DETAILED DESCRIPTION

Figure 1A:
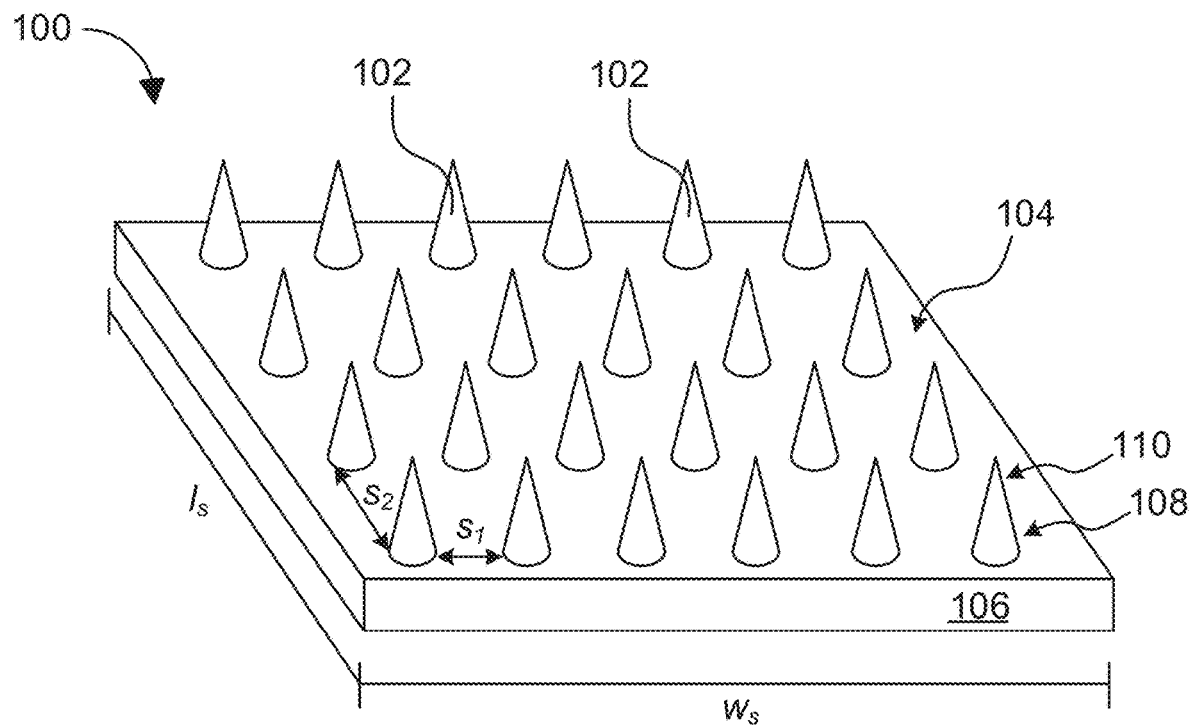
FIGS. 1A-1B depict isometric and side views, respectively, of a microneedle patch comprising a plurality of microneedles on a surface of a scaffold, according to one embodiment.

Specific, non-limiting embodiments of the present invention will now be described with reference to the figures, in which reference numerals denoting like features are labeled similarly. It should be understood that particular features and aspects of any embodiment disclosed herein may be used and/or combined with particular features and aspects of any other embodiment disclosed herein. It should also be understood that such embodiments are by way of example and are merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

Unless the context requires otherwise, throughout the present specification and claims, the word "comprise" and variations thereof, such as, "comprises" and "comprising" are to be construed in an open, inclusive sense, that is as "including, but not limited to". The use of all examples, illustrations, and/or exemplary language ("e.g.", "such as", etc.) herein does not impose a limitation on the scope of the invention unless otherwise specified. Furthermore, recitation of numeric ranges of values throughout the specification is intended to serve as a shorthand notation of referring individually to each separate value falling within the range inclusive of the values defining the range, and each separate value is incorporated in the specification as it were individually recited herein. Additionally, the singular forms "a", "an" and "the" include plural referents unless the context clearly dictates otherwise.

As discussed previously, patch testing is commonly used to identify agents that a person's skin is allergic to. However, conventional patch testing usually takes a long period of time, may result in inaccurate characterization of the degree of the allergic response, and is expensive. Intradermal injection of an agent via a hypodermic needle is another method commonly used to assess a person's response to said agent; yet, use of hypodermic needles is often painful, difficult to control, and inconvenient for self-administration. Moreover, conventional microneedle patches for transdermal delivery of an agent vary widely in their ability to penetrate mammalian skin, degree of biocompatibility, and ability to control the release of the agent.

Embodiments described herein are directed to a simple, inexpensive, and novel microneedle patch for diagnosis of allergies to an agent. In particular, this microneedle patch provides a safe and easy way to deliver an agent (or agents) to the dermal layers of a person's skin. The microneedle patch may comprise a plurality of microneedles coupled to a surface of a scaffold (which may also be referred to herein as a "patch scaffold" or "pedestal"). The microneedles and scaffold may each be fabricated using polyvinylpyrrolidone (PVP) and one or more additional copolymers selected from the group consisting of maltose, leucine, and dileucine. The microneedles may additional comprise an agent disposed therein and/or coated thereon.

Use of the novel microneedle patch, as disclosed herein, may involve pressing the microneedle patch to a person's skin such that each of the microneedles loaded with an agent pierces the skin. In some embodiments, the microneedles may have dimensions so as to pierce the skin about 50 μm to about 1000 μm deep. The biocompatible composite material of the microneedles dissolves upon insertion into the skin, thereby delivering the agent at a precise, controlled location within the dermal layers of the skin. The location of the agent within each microneedle may also be tailored according to the methods disclosed herein, thereby allowing for controlled rates of agent release.

If the person being tested has an allergic response to an agent present in the microneedles, the skin will respond rapidly, such as by an increase in temperature. The "hot spots" (e.g., areas of increased temperature) caused by allergic responses may be detected by a sensor, such as a thermal or image sensor. For instance, in one embodiment, an infrared (IR) image can be captured following the microneedle injection to identify the hot spots. By loading at least one agent into the microneedle in an array, a whole library of agents may be tested in a single assay.

In some embodiments, the microneedle patch, as disclosed herein, may be useful for testing a person's response to a cosmetic or preparation. Cosmetic preparations encompasses a heterogeneous group of often complex products. The ingredients in the cosmetic preparations often include active materials as well as other various natural and/or synthetic excipients, such as preservatives, buffers, matrix components and fragrances. Such combination of active materials and excipients may cause mild to severe allergic reactions, such as contact dermatitis in many people, and particularly immunocompromised people. The complexity of the allergic reactions becomes multifaceted when considering alleged natural topical formulations or cosmetics with more complicated formulations. It is therefore beneficial to rigorously test cosmetic preparations prior to their potential application since they not only encompass a wide range of ingredients, but are also formulated to produce a wide range of products. The microneedle patch, as disclosed herein, is particularly suited for such use.

The microneedle patch can also be used to delivery agents to a skin, for cosmetic or pharmaceutical purposes. In this respect, the patch can be provided in the form of a facial mask (or part of a facial mask), for example. The cosmetic or pharmaceutical agents packaged in the microneedle patch can be delivered into the skin, rendering desired effects on the skin. The cosmetic or pharmaceutical agents include, without limitation, agents capable of improving the look, nutrition, or health of the skin or ameliorating a condition or disease of the skin.

Figure 1B:
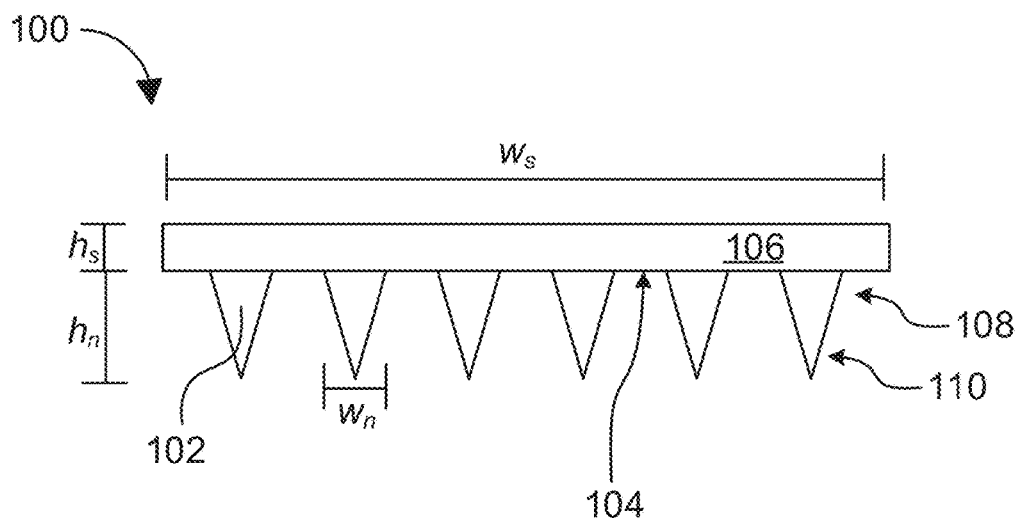

Referring now to FIGS. 1A-1B, an isometric and side view, respectively, of an exemplary microneedle patch 100 is shown in accordance with one embodiment. The microneedle patch 100 may be implemented in combination with other devices/features/components described herein, such as those described with reference to other embodiments and FIGS. The microneedle patch 100 may also be used in various applications and/or in permutations, which may or may not be noted in the illustrative embodiments described herein. For instance, the microneedle patch 100 may include more or less features/components than those shown in FIG. 1, in some embodiments. Moreover, the microneedle patch 100 is not limited to the size, shape, number of components, etc. specifically shown in FIG. 1.

As shown in FIGS. 1A-1B, the microneedle patch 100 comprises a plurality of microneedles 102 disposed on a surface 104 of a scaffold 106. Each microneedle comprises a base/stem portion 108 located proximate to the base of the microneedle 102, where the base refers to the point of attachment of the microneedle to the surface 104 of the scaffold. Each microneedle 102 also comprises a tip portion 110 located proximate to the tip of the microneedle 102 and further located distal to the base/stem portion 108.

The number of microneedles 102 disposed on the surface of the scaffold 106 may be selected based on a desired application. In some embodiments, the microneedle patch 100 may include at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, at least 32, at least 34, at least 36, at least 38, at least 40, etc. microneedles 102. In some embodiments, the number of microneedles 102 may be in a range including and between any two of the following: 1 microneedle, 2 microneedles, 3 microneedles, 4 microneedles, 5 microneedles, 6 microneedles, 7 microneedles, 8 microneedles, 9 microneedles, 10 microneedles, 11 microneedles, 12 microneedles, 13 microneedles, 14 microneedles, 15 microneedles, 16 microneedles, 17 microneedles, 18 microneedles, 19 microneedles, 20 microneedles, 21 microneedles, 22 microneedles, 23 microneedles, 24 microneedles, 25 microneedles, 26 microneedles, 27 microneedles, 28 microneedles, 29 microneedles, 30 microneedles, 31 microneedles, 32 microneedles, 34 microneedles, 35 microneedles, 36 microneedles, 37 microneedles, 38 microneedles, 39 microneedles, 40 microneedles, 45 microneedles, 50 microneedles, 60 microneedles, 65 microneedles, 70 microneedles, 75 microneedles, 80 microneedles, 85 microneedles, 90 microneedles, 95 microneedles, 100 microneedles, 150 microneedles, 200 microneedles, 250 microneedles, 300 microneedles, 350 microneedles, 400 microneedles, 450 microneedles, 500 microneedles, 600 microneedles, 700 microneedles, 800 microneedles, 900 microneedles, 1000 microneedles, 1200 microneedles, 1400 microneedles, 1600 microneedles, 1800 microneedles, and 2000 microneedles. In one embodiment, the microneedle patch 100 comprises about 24 microneedles 102.

In some embodiments, the microneedle patch 100 comprises a density of about 25 microneedles to about 625 microneedles per $cm^2$. In some embodiments, density of the microneedles may be in a range including and between any two of the following: $25/cm^2$, $50/cm^2$, $75/cm^2$, $100/cm^2$, $125/cm^2$, $150/cm^2$, $175/cm^2$, $200/cm^2$, $225/cm^2$, $250/cm^2$, $275/cm^2$, $300/cm^2$, $325/cm^2$, $350/cm^2$, $375/cm^2$, $400/cm^2$, $425/cm^2$, $450/cm^2$, $475/cm^2$, $500/cm^2$, $525/cm^2$, $550/cm^2$, $575/cm^2$, $600/cm^2$, and $625/cm^2$.

In some embodiments, the microneedle patch 100 may comprise from 1 to 50 rows, 1 to 40 rows, 1 to 30 rows, 1 to 20 rows, 1 to 10 rows, 1 to 9 rows, 1 to 8 rows, 1 to 7 rows, 1 to 6 rows, 1 to 5 rows, 1 to 4 rows, 1 to 3 rows, 1 to 2 rows, or 1 row of microneedles 102. Each row may further comprise from 1 to 50 microneedles, from 1 to 40 microneedles, from 1 to 30 microneedles, from 1 to 20 microneedles, from 1 to 10 microneedles, from 1 to 9 microneedles, from 1 to 8 microneedles, from 1 to 7 microneedles, from 1 to 6 microneedles, from 1 to 5 microneedles, from 1 to 4 microneedles, from 1 to 3 microneedles, from 1 to 2 microneedles, or 1 microneedle.

In some embodiments, the spacing, $s_1$, between the microneedles 102 in a row may be in a range from about 100 to about 1000 μm. In some embodiments, the spacing, $s_1$, between the microneedles 102 in a row may be in a range including and between any two of the following: 100 μm, 125 μm, 150 μm, 175 μm, 200 μm, 225 μm, 250 μm, 275 μm, 300 μm, 325 μm, 350 μm, 375 μm, 400 μm, 425 μm, 450 μm, 475 μm, 500 μm, 525 μm, 550 μm, 575 μm, 600 μm, 725 μm, 750 μm, 775 μm, 800 μm, 925 μm, 950 μm, 975 μm, and 1000 μm. In some embodiments, the spacing, $s_1$, between the microneedles 102 in at least one row, a plurality of the rows, or each row may be about equal. In other embodiments, the spacing, $s_1$, between the microneedles 102 in one row may be different than the spacing between the microneedles 102 in at least another row.

In some embodiments, the spacing, $s_2$, between at least two rows may be in a range from about 100 to about 1000 μm. In some embodiments, the spacing, $s_2$, between at least two rows may be in a range including and between any two of the following: 100 μm, 125 μm, 150 μm, 175 μm, 200 μm, 225 μm, 250 μm, 275 μm, 300 μm, 325 μm, 350 μm, 375 μm, 400 μm, 425 μm, 450 μm, 475 μm, 500 μm, 525 μm, 550 μm, 575 μm, 600 μm, 725 μm, 750 μm, 775 μm, 800 μm, 925 μm, 950 μm, 975 μm, and 1000 μm. In some embodiments, the spacing, $s_2$, between each row may be about equal. In other embodiment, the spacing, $s_2$, between the rows may be different.

In some embodiments, the microneedles 102 may be spaced uniformly (e.g., at approximately equal intervals) on the surface of the scaffold 106. However, in other embodiments, e.g., as shown in the isometric view of FIG. 2, the microneedle patch 100 may comprise two or more discrete areas 202, each of which comprises a plurality of microneedles 102. In one such exemplary embodiment, the spacing, $s_3$, between each discrete area 202 may be about uniform (equal), and the spacing, $s_4$, between each microneedle 102 in a particular discrete area 202 may be about uniform (equal), provided that $s_3$ is about equal to or greater than $s_4$.

Figure 2:
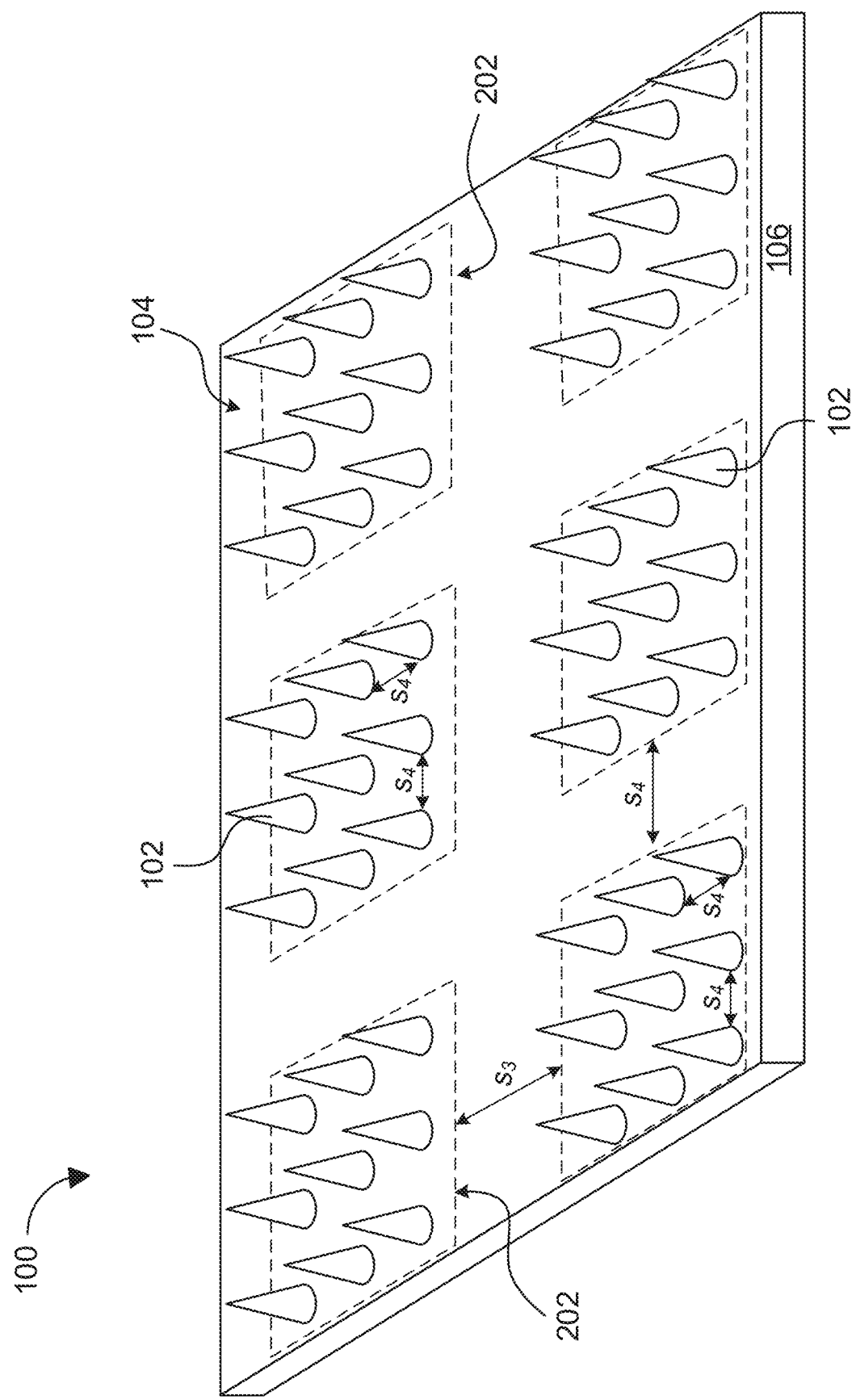
FIG. 2 depicts an isometric view of a microneedle patch comprising discrete areas of microneedles, according to one embodiment.

The microneedles 102, e.g., as shown in FIGS. 1A-1B and 2, may comprise a substantially pyramidal or conical shape. Others microneedle shapes may be suitable as would become apparent to one skilled in the art upon reading the present disclosure. For instance, in one embodiment, each microneedle 102 may comprise a substantially cylindrical shape towards the base/stem portion 108 thereof that transitions to a substantially pyramidal shape (e.g., a pointed portion) near the tip portion 110 thereof. Moreover, the microneedles 102 are not limited to sharp pointed needles, and may thus include blunt tips.

In some embodiments, the microneedles 102 may each have a maximum length (height, $h_n$) ranging from about 20 μm to about 1000 μm, preferably in a range from about 50 μm to about 1000 μm, and more preferably in a range from about 100 μm to about 1000 μm. In some embodiments, the microneedles 102 may each have a maximum width, $w_n$, ranging from about 10 μm to about 500 μm. In some embodiments, the microneedles 102 may each have a high aspect ratio ranging from about 1:1 to 20:1, where the aspect ratio refers to the ratio of a microneedle's maximum length (height, $h_n$) relative to its maximum width.

Figure 3:
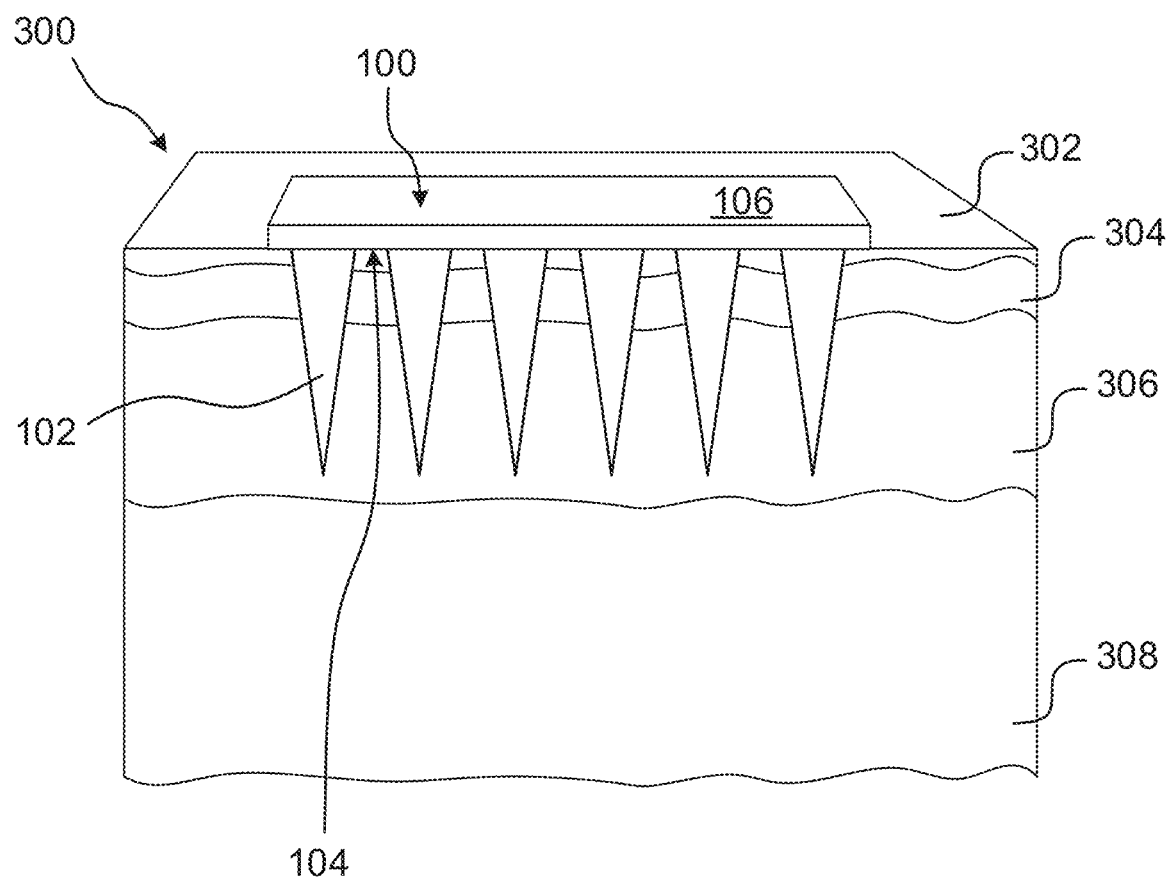
FIG. 3 depicts a microneedle patch applied to mammalian skin, according to one embodiment.

In some embodiments, the microneedles 102 are configured to pierce the skin for the percutaneous administration of an agent. In particular embodiments, the microneedles are configured to piece the skin at a depth of about 50 μm to 1000 μm. FIG. 3 provides an exemplary embodiment of a microneedle patch 100 piercing mammalian (e.g., human) skin 300 to reach the dermis layer thereof is shown in FIG. 3. As shown in FIG. 3, the skin 300 comprises the following layers: stratum corneum 302 at a depth greater than 0 μm to about 20 μm); epidermis 304 at a depth from about 20 μm to about 100 μm; dermis 306 at a depth from about 100 μm to about 1000 μm, and subcutis (hypodermis) 308 at a depth greater than about 1000 μm. The scaffold 104 of the microneedle patch may preferably contact (and temporarily and removably adhere to) the outermost layer of the skin 300 (e.g., the stratum corneum 302), while the microneedles 102 pierce the skin 300 such that the tips of said microneedles 102 are positioned within (and do not extend deeper than) the dermis layer 306 of the skin 300.

The microneedles 102, e.g., as shown in FIGS. 1A-1B, 2, and 3, are each comprised of a composite material. Additionally, the microneedles 102 may each comprise an agent disposed within and/or coated on at least a portion of the composite material.

In some embodiments, the composite material of each of the microneedles 102 is configured to dissolve after a predetermined period of time after insertion into mammalian skin, and thereby deliver the agent thereto. In some embodiments, the composite material is biocompatible and/or biodegradable. In some embodiments, the composite material comprises polymer components that are approved by the Federal Drug Administration (FDA) and/or are GRAS (generally recognized as safe) polymers.

In some embodiments, the composite material comprises polyvinylpyrrolidone (PVP) and one or more additional copolymers selected from the group consisting of maltose, leucine, and dileucine. In one embodiment, the composite material comprises at least PVP and maltose. In one embodiment, the composite material comprises PVP, maltose, and one or more additional copolymer components selected from leucine and dileucine. In one embodiment, the composite material comprises at least PVP, maltose, and leucine. In one embodiment, the composite material comprises at least PVP, maltose, and dileucine. In one embodiment, the composite material comprises PVP, maltose, leucine, and dileucine.

In some embodiments, the composite material comprises about 50 to about 90 wt. %, and more preferably about 70 to about 85 wt. %, PVP. In one embodiment, the composite material comprises about 70 wt. % PVP. In one embodiment, the composite material comprises about 80 wt. % PVP. In one embodiment, the composite material comprises about 85 wt. % PVP.

In some embodiments, the composite material comprises about 0 to about 30 wt. %, and preferably about 10 to about 20 wt. %. maltose. In one embodiment, the composite material comprises about 10 wt. % maltose. In one embodiment, the composite material comprise about 20 wt. % maltose.

In some embodiments, the composite material comprises about 0 to about 20 wt. %, and preferably about 2.5 to about 10 wt. %, leucine. In one embodiment, the composite material comprises about 2.5 wt. % leucine. In one embodiment, the composite material comprises about 5 wt. % leucine. In one embodiment, the composite material comprises about 10 wt. % leucine.

In some embodiments, the composite material comprises about 0 to about 20 wt. %, and preferably about 2.5 to about 10 wt. %, dileucine. In one embodiment, the composite material comprises about 2.5 wt. % dileucine. In one embodiment, the composite material comprises about 5 wt. % dileucine. In one embodiment, the composite material comprises about 10 wt. % dileucine.

In one embodiment the composite material comprises about 70 to about 90 wt. % PVP; about 10 to 20 wt. % maltose; about 2.5 to about 10 wt. % leucine; and about 2.5 to about 10 wt. % dileucine. It has been found that the composite material with such combination of polymeric components yields microneedles 102 that have a desired durability and tensile strength to penetrate mammalian skin, and further are able to quickly dissolve upon insertion into the skin.

In one embodiment, the composite material comprises about 70 wt. % PVP; about 10 wt. % maltose; about 10 wt. % leucine; and about 10 wt. % dileucine. In one embodiment, the composite material comprises about 70 wt. % PVP; about 20 wt. % maltose; about 5 wt. % leucine; and about 5 wt. % dileucine. In one embodiment, the composite material comprises about 80 wt. % PVP; about 10 wt. % maltose; about 5 wt. % leucine; and about 5 wt. % dileucine. In one embodiment, the composite material comprises about 85 wt. % PVP; about 10 wt. % maltose; about 2.5 wt. % leucine; and about 2.5 wt. % dileucine.

In some embodiments, the composite material may comprise one or more additional components such as chitosan. For instance, in one embodiment, the composite material may comprise PVP, chitosan, and one or more copolymers selected from maltose, leucine, and dileucine.

In some embodiments, the composite material may exclude metallic or other polymer materials aside from PVP, maltose, leucine, and dileucine. For instance, inclusion of polyethylene glycol (PEG) into the composite material may make said mixture more pliable for molding purposes (e.g., in the preparation of the microneedle structures), yet ultimately result in microneedles that are less durable with insufficient tensile strength to penetrate mammalian skin.

As noted above, each of the microneedles 102 comprises an agent that is released upon penetration and subsequent dissolution of the microneedles within mammalian skin. In some embodiments, the agent may comprise an active agent. In one embodiment, the agent may comprise an antigen for fungi, bacteria, house dust, atopic dermatitis, pollen species (e.g., cedar, cypress, ragweed, mugwort, birch, rice plants, etc.), food species (e.g., eggs, tree nuts, peanuts, soy, wheat, milk, meat, rice, beans, seafood, shellfish, etc.), pet dander, textiles, detergent preparations (e.g., laundry detergents, softeners, etc.), cosmetic preparations, the tuberculin reaction, particular drugs, etc.

In one embodiment, the agent may comprises a cosmetic preparation. Cosmetic preparations may be formulated as lotions, creams/emulsions, lotions, ointments, pastes, suspension, powders, gels, sticks, aerosols, etc. Further, cosmetic preparations may include, but are not limited to facial makeup preparations (e.g., rouge, eye shadow, mascara, eye liner, lipstick, lip gloss, lip liner, foundation, etc.), skin care preparations (skin moisturize and lotion, skin cleanser, sunscreen, etc.), hair care preparations (e.g., shampoo, conditioner, leave in hair care/styling products, hairspray, hair gel, hair dyes, etc.), nail care preparation (e.g., nail polish, nail polish remover, etc.), perfume, colognes, etc. In one embodiment, a cosmetic preparation is as defined by the FDA, and constitutes any article intended to be rubbed, poured, sprinkled, or sprayed on, introduced into, or otherwise applied to the human body for cleansing, beautifying, promoting attractiveness, or altering the appearance.

In one embodiment, the agent may comprise a drug. A drug may comprises a protein, antibody, chemical compound, DNA/RNA, etc. In one embodiment, a drug is as defined by the FDA, and constitutes any articles intended for use in the diagnosis, cure, mitigation, treatment, or prevention of disease, as well as articles (other than food) intended to affect the structure or any function of the body of man or other animals.

In one embodiment, the agent may comprise a vaccine.

In some embodiments, at least two of the microneedles 102 may comprises the same agent as one another. For instance, in one embodiment, at least two of the microneedles 102 may comprise the same cosmetic preparation. In some embodiments, a plurality of the microneedles 102 may comprise the same agent as one another. In some embodiments, each of the microneedles 102 may comprise the same agent as one another.

In some embodiments, at least two of the microneedles 102 may comprises different agents as one another. For instance, in one embodiment, at least two of the microneedles 102 may comprise different cosmetic preparations (e.g., a makeup preparation versus a hair care preparation; different makeup preparations such as an eyeshadow versus a lipstick, or two different eyeshadows, etc.) In some embodiments, a plurality of the microneedles 102 may comprise different agents as one another. In some embodiments, each of the microneedles 102 may comprise different agents as one another.

In some embodiments, a first plurality of the microneedles 102 may comprise a different agent from the agent associated with at least a second plurality of the microneedles 102. For instance, with reference to FIG. 2, at least two of the discrete areas 202 of microneedles 102 may comprises different agents from one another.

In some embodiments, the concentration of the agent in each microneedle is sufficient to induce an allergic reaction but not so high as to irritate and cause a false-positive reaction in the mammalian skin to which the agent is delivered. In some embodiments, the agent is present in each microneedle in an amount ranging from about 0.01 wt. % to about 50 wt. %. In some embodiments, each microneedle comprises a weight ratio of the agent to the composite material ranging from about 1:1 to about 1:1000.

Figure 4A:
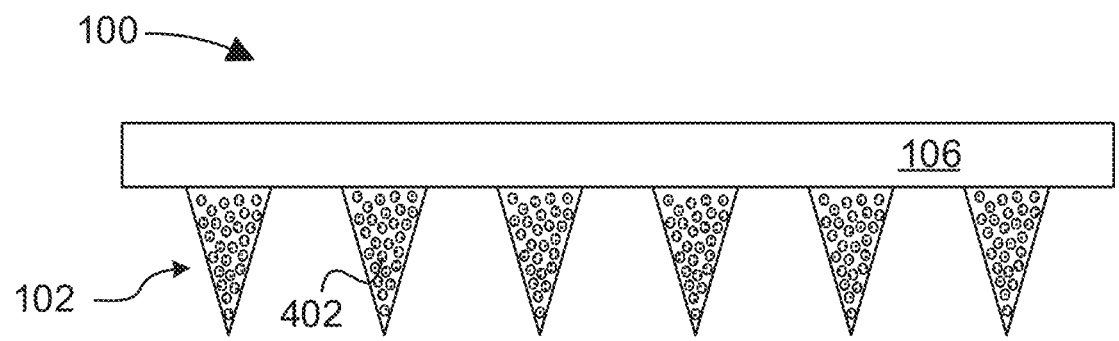
FIGS. 4A-4E depict side view of a microneedle patch comprising a plurality of microneedles and an agent associated therewith, according to various embodiments.
Figure 4B:
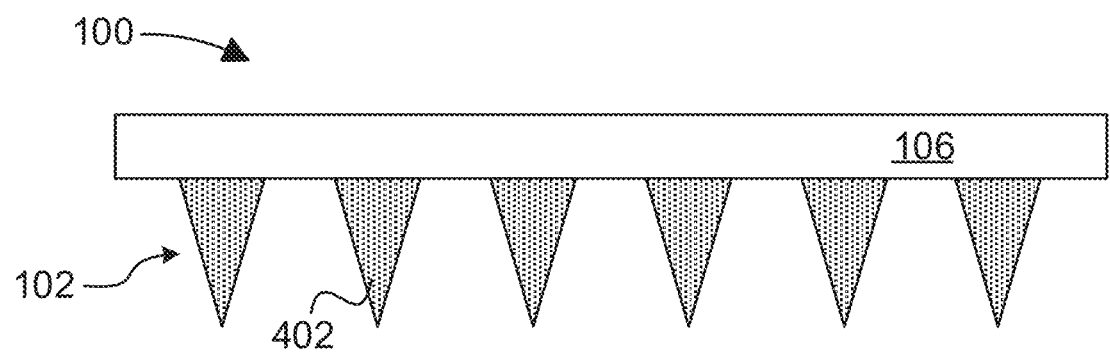
Figure 4C:
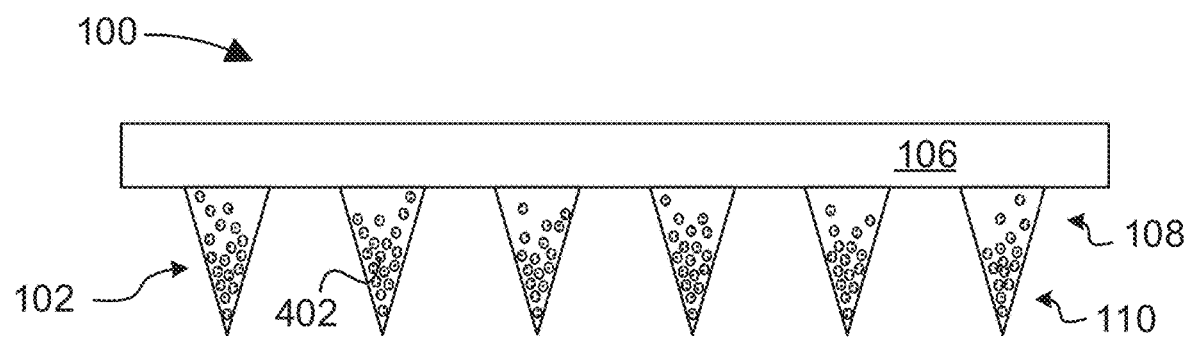

The aforementioned agent may be disposed within and/or coated on a portion of each microneedle 102 as shown in the exemplary embodiments of FIGS. 4A-4C. In the embodiment of FIG. 4A, the agent 402 may be dispersed within the composite material of each microneedle 102. In one such embodiment, the agent may be uniformly dispersed within the composite material of each microneedle 102.

In the embodiment of FIG. 4B, the agent 402 may be coated on the entire exterior periphery of the microneedle 102. However, in alternative embodiments, the agent 402 need not be coated on the entire periphery of the microneedle 102, but may be coated on one or more portions thereof. Further, the agent 402 may be uniformly dispersed within the composite material of each microneedle 102, as well as coated on at least a portion of the exterior periphery thereof, in some embodiments.

Figure 4D:
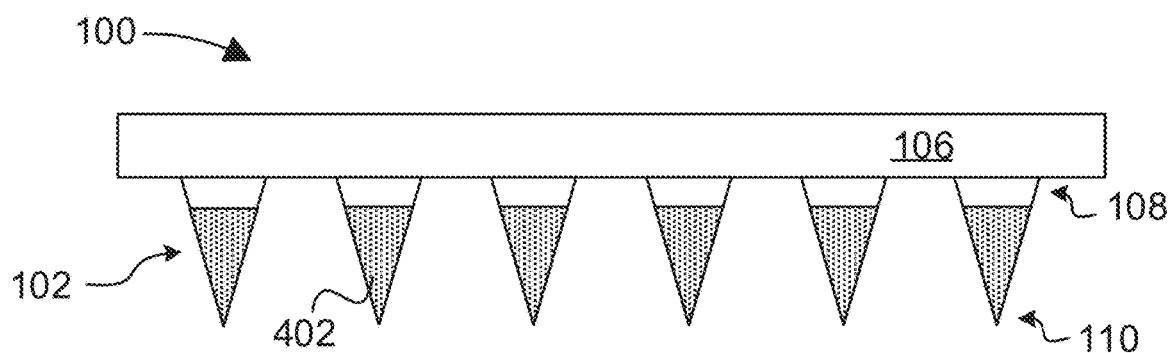

In the embodiments of FIG. 4C-4D, the tip portion 110 of each microneedle 102 may comprise a higher concentration of the agent 402 as compared to the base/stem portion 108 thereof. It is of note that this concentration gradient may arise where the base/stem portion 108 of each microneedle 102 either comprises no agent 402, or comprises the agent 402 at a lower concentration than the tip portion 110. Further, this concentration gradient may be gradual or abrupt in some embodiments.

As shown in the embodiment of FIG. 4C, the agent 402 may be dispersed predominantly within the tip portion 110 of each microneedle 102 (e.g., within the composite material of the tip portion 110) such that there is a larger agent 402 concentration in said tip portion 110 as compared to the base/stem portion 108 of the microneedle 102. In such an embodiment, a majority, substantially all, or all of the agent 402 associated with a microneedle 102 may be dispersed within the tip portion 110 of the microneedle 102.

In the embodiment of FIG. 4D, the agent 402 may be coated predominantly on the tip portion 110 of the microneedle 102 (e.g., coated on the composite material of the tip portion 110) such that there is a larger agent 402 concentration in said tip portion 110 as compared to the base/stem portion 108 of the microneedle 102. In such an embodiment, a majority, substantially all, or all of the agent 402 associated with a microneedle 102 may be coated on at least a portion of the exterior surface of the tip portion 110 of the microneedle 102. In one particular embodiment, the entire periphery of the tip portion 110 of each microneedle 102 may be coated with the agent 402. In some embodiments, the agent 402 may be predominantly dispersed within the tip portion 110 of each microneedle 102 (e.g., within the composite material of the tip portion 110), as well as predominantly coated on at least an exterior surface of said tip portion 110.

Figure 4E:
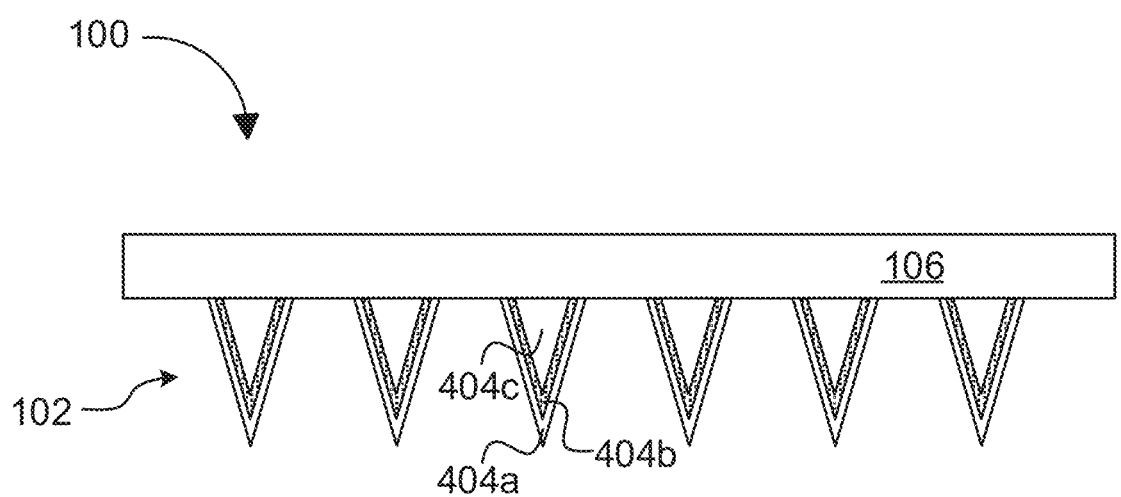

In the embodiment of FIG. 4E, each microneedle 102 may comprise a plurality of layers, where at least some of the alternating layers comprise different concentrations of the agent 402. For instance, each microneedle 102 may comprise at least three layers: a first layer 404a, a second layer 404b, and a third layer 404c, where the second layer is 404b is positioned between the first and third layers 404a, 404c. While each of the layers may be comprised of a composite material, as discussed previously, the second layer 404b may comprise a higher concentration of the agent 402 than the first layer 404a and/or the third layer 404c. In one instance, the second layer 404b may comprise a higher concentration of the agent 402 than at least the first layer 404a. In one instance, the second layer 404b may comprise a higher concentration of the agent 402 than at least the third layer 404c. In one instance, the second layer 404b may comprise a higher concentration of the agent 402 than the first layer 404a and the third layer 404c.

Moreover, in instances where the second layer 404b comprises a higher concentration of the agent 402 than the first and third layers 404a, 404c, the first layer 404a may have the same or a different agent concentration than the third layer 404c. For example, the first and third layers 404a, 404c may comprise equal concentrations of the agent 402, which is lower than the concentration of the agent 402 in the second layer 404b. Similarly, the second layer 404b may comprise a predetermined amount of the agent 402, whereas the first and third layer 404a, 404c comprise none, or substantially none, of the agent 402. Alternatively, the second layer 404b may comprise a higher concentration of the agent 402 than the first and third layers 404a, 404c, however the first layer 404a may comprise a higher (or lower) agent concentration than the third layer 404c.

In other instances, the concentration of the agent 402 may decrease from the first layer 404a to the third layer 404c (e.g., the second layer 404b may comprise a lower agent concentration than the first layer 404a and a higher agent concentration than the third layer 404c). In yet more instances, the concentration of the agent 402 may increase from the first layer 404a to the third layer 404c (e.g., the second layer 404b may comprise a lower agent concentration than the third layer 404c and a higher agent concentration than the first layer 404a).

It is of note that the number and configuration of the layers is not limited by the schematic of FIG. 4E. For example, in further instances, each microneedle may comprise a fourth layer adjacent the third layer 404c, and a fifth layer adjacent the fourth layer such that the fourth layer is positioned between the third layer 404c and the fifth layer. The fourth and fifth layer may independently comprise an agent concentration that is the same or different than any of the other layers. In one exemplary instance, the second layer 404b and the fourth layer may each comprise an agent concentration that is higher than the first and third layers 404a, 404c. In one such instance, the agent 402 may be present in the second layer 404b and the fourth layer, yet absent, or substantially absent, in the first and third layers 404a, 404c.

In some embodiments, the scaffold 106 is configured to temporarily and removably contact the outer layer of mammalian skin (e.g., the stratum corneum) upon engagement of the microneedle patch 100 therewith, and particularly when the microneedles 102 have pierced the skin to a depth of between 50 μm to 1000 μm (see, e.g., FIG. 3). In such embodiments, the surface 104 of the scaffold 106 to which the microneedles 102 are coupled may contact the outer layer of the skin. Accordingly, the scaffold 104 may preferably be comprised of a flexible material configured to provide adequate skin adhesion and/or stress dispersion.

In some embodiments, the scaffold 106 may comprise one or more of the same materials as the microneedles 102. In one embodiment, the scaffold 106 may comprise the same composite material as the microneedles 102. For instance, in one embodiment, the scaffold may comprise polyvinylpyrrolidone (PVP) and one or more additional copolymers selected from the group consisting of maltose, leucine, and dileucine. In other embodiments, the scaffold 106 may comprises one or more materials that are different than those of the microneedles 102.

In some embodiments, the microneedle patch 100 may be a monolithic structure, such that the scaffold 106 and microneedles 102 are all comprised of a single material, such as a composite material comprising PVP and one or more additional copolymers selected from the group consisting of maltose, leucine, and dileucine. Formation of such a monolithic structure may involve combining PVP, the one or more additional copolymers, and an agent disclosed herein to form a mixture, and subsequently adding said mixture to a mold comprising the desired shape of the microneedle patch 100. Such process may result in the agent being disposed in the scaffold 106 as well as the microneedles 102. However, the microneedle patch 100 may be formed by other processes that result in the agent being disposed in and/or the microneedles 102, but not disposed in the scaffold 106.

In some embodiments, the microneedle patch 100 is not a monolithic structure such that the scaffold 106 is formed separately and/or is a separate component relative to the microneedles 102. In one such embodiment, the microneedles 102 may be directly attached/coupled to the surface 104 of the scaffold 102. In one such embodiment, the microneedles 102 may be directly attached/coupled to the surface 104 of the scaffold 102, and do not extend within a central region of the scaffold 102. Moreover, in embodiments in which the microneedle patch 100 is not a monolithic structure, the scaffold 106 may still comprise one or more of the same materials as the microneedles 102. Alternatively, in embodiments in which the microneedle patch 100 is not a monolithic structure, the scaffold may comprise one or more materials that are different from those of the microneedles 102. For instance, in one such embodiment, the agent may be localized in the microneedles 102 and not present in the scaffold 106.

In some embodiments, the dimensions of the scaffold 106 (e.g., the width, $w_s$, and/or length, $l_s$) may be tailored to a include a certain number and/or configuration of microneedles 102 for a specific application. Similarly, the height, $h_s$, of the scaffold 106 may also be tailored, as would be appreciated by a skilled artisan upon reading the present disclosure, to provide a desired level of support and/or flexibility thereto.

In some embodiments, the surface 104 of the scaffold 106 configured to contact mammalian skin may comprise an optional coating thereon, where said option coating comprises a material configured to provide suitable skin adhesion and/or stress dispersion. In one embodiment, the microneedles 102 may be directly coupled to the optional coating. In another embodiment, the optional coating may substantially surround the base of each of the microneedles 102, such that microneedles 102 are directly coupled to the surface 104 of the scaffold 106.

As disclosed herein, the microneedles 102 of the microneedle patch 100 may be configured to pierce mammalian skin, preferably to a depth of about 50 μm to 1000 μm, and subsequently dissolve to release agents disposed therein and/or coated thereon. An allergic response to an agent may be identified by an increase in the temperature of the subject's skin at the location where said agent was delivered. Accordingly, in one embodiment, determining a subject's allergic response to agents comprised in the microneedles 102 may comprise determining whether the location at which each agent was delivered increases in temperature. In some embodiments, the temperature increase may need to be at least equal to or exceed a threshold value to be identified as an allergic response. This threshold may be set based on the identity of the agents and/or characteristics of the subject (e.g., age, weight, etc.).

Figure 5A:
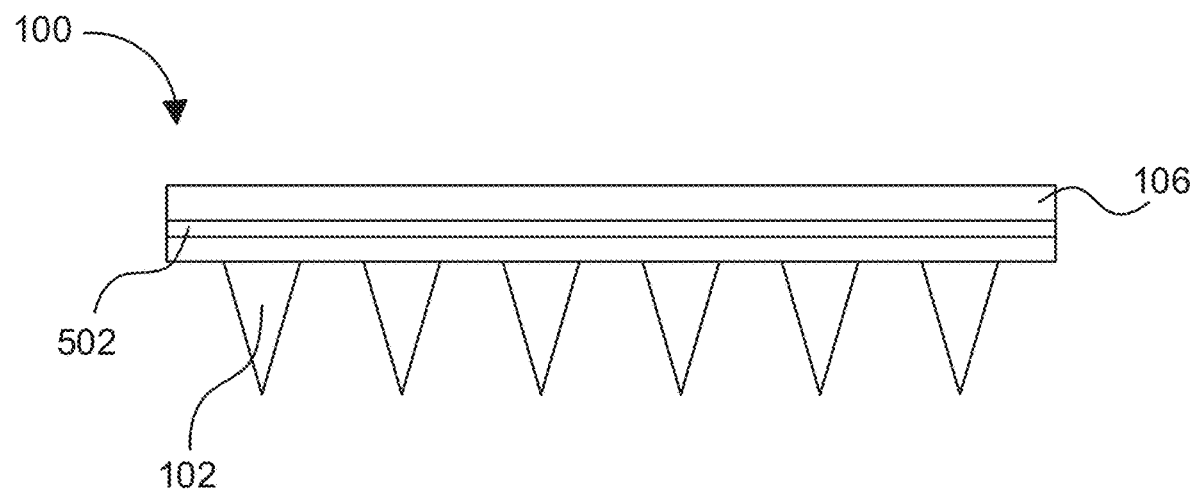
FIGS. 5A-5B depict a side view and top view, respectively, of a microneedle patch comprising a detector device configured to detect an allergic response, according to various embodiments.

In some embodiments, the aforementioned temperature increase, and thus allergic response, may be determined by a detector operatively coupled to the microneedle patch 100. FIG. 5A provides a side view of the microneedle patch 100, where such a detector 502 is located in the scaffold 106, according to one embodiment. The detector 502 may comprise one or more sensors, each of which is configured to measure/detect a temperature increase (i.e., the hot spots caused by an allergic response to an agent). The one or more sensors may independently be a thermal or image sensor. In one embodiment, each of the sensors of the detector 502 may be an image sensor configured to capture infrared (IR) images.

Figure 5B:
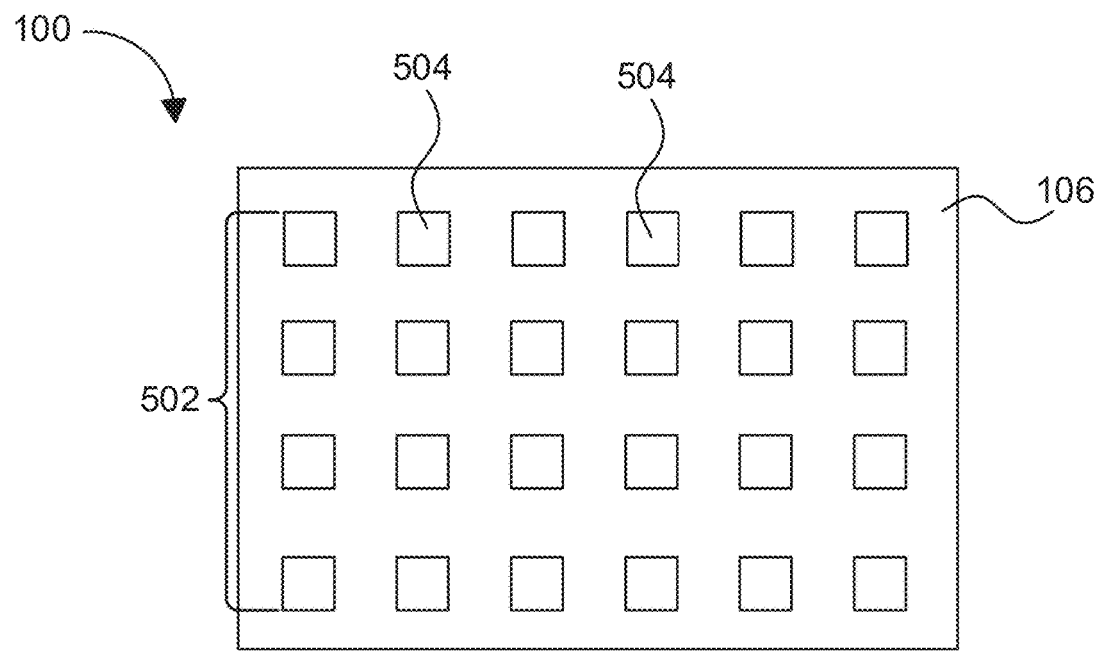

FIG. 5B provides a top down view of the microneedle patch 100, were the detector 502 comprises a sensor 504 above each microneedle 102, according to one embodiment. As noted above, each of the sensors 504 may independently be a thermal or image sensor. In one embodiment, each of the sensors 504 may be an IR image sensor.

In some embodiments, a detector configured to determine the aforementioned temperature increase, and thus allergic response, may be associated with an external device, and not physically coupled to the microneedle patch 100. In such embodiments, the external device comprising the detector may be brought within a predetermined proximity to the skin after application of the microneedle patch to determine the presence of an allergic response.

EXAMPLES

Several illustrative examples for making and using microneedle patches, as disclosed herein, are described below. It is important to note that these illustrative examples are in no way limiting, and are provided by way of example only.

Figure 6:
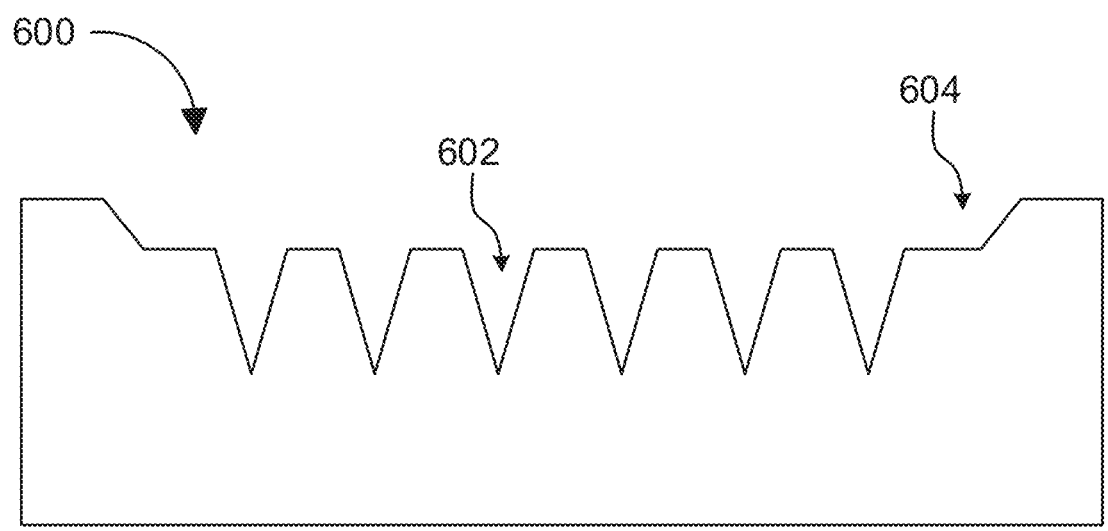
FIG. 6 depicts a mold for preparation of a microneedle patch, according to one embodiment.

Example 1: Method of Making a Microneedle Patch Comprising a Plurality of Microneedles, Each Microneedle Comprising an Agent Dispersed Therein A poly dimethyl siloxane (PDMS) mold, e.g., as shown in the embodiment of FIG. 6, was utilized for microneedle preparation according to this first method. The mold was previously etched with stainless steel microneedles fabricated by laser cutting techniques.

A first mixture of PVP, maltose, leucine, and dileucine was prepared as a slurry to form the composite material of the microneedles. The weight ratio of PVP to the combination of maltose, leucine, and dileucine was about 2:1 (PVP:maltose+leucine+dileucine=2:1) to give stability to the PVP. An agent was added to the first mixture, where the weight ratio of the agent to the mixture of PVP, maltose, leucine, and dileucine was about 1:4. ratio. Approximately 25 to 30 µl of the first mixture was applied to the PDMS mold and allowed to dry in a desiccator attached to a vacuum pump for about 5 to 10 mins to form the microneedles.

A second mixture of PVP, maltose, leucine, and dileucine was prepared as a slurry to form the composite material of the scaffold (or pedestal). This second mixture did not include any agent. Approximately 150 to 200 µl of this second mixture was applied to the PDMS mold over the preformed microneedles.

The mold comprising both the first and second mixtures was then dried overnight in a sterile environment at room temperature, thereby forming the microneedle patch comprising the agent dispersed in the each of the microneedles. An example of a microneedle patch formed via this first method may be found, e.g., in FIGS. 4A and 4C.

Example 2: Method of Making a Microneedle Patch Comprising a Plurality of Microneedles, Each Microneedle Comprising an Agent Coated on the Periphery Thereof A poly dimethyl siloxane (PDMS) mold, e.g., as shown in the embodiment of FIG. 6, was also utilized for microneedle preparation according to this second method. As noted above, the mold was previously etched with stainless steel microneedles fabricated by laser cutting techniques.

Approximately 10 µl of the agent was initially poured into the etched grooves of the PDMS mold and allowed to dry under vacuum for 3 to 5 minutes in a suitable solvent. A mixture of PVP, maltose, leucine, and dileucine was then prepared as a slurry to form the composite material of the microneedles. The weight ratio of PVP to the combination of maltose, leucine, and dileucine was about 2:1 (PVP:maltose+leucine+dileucine=2:1). Approximately 120 µl of the slurry was applied to the PDMS mold comprising the agent, and the mold was allowed to dry in a desiccator attached to a vacuum pump for about 5 to 10 mins to form the microneedles.

A second mixture of PVP, maltose, leucine, and dileucine was prepared as a slurry to form the composite material of the scaffold (or pedestal). This second mixture did not include any agent. Approximately 150 to 200 µl of this second mixture was applied to the PDMS mold over the preformed microneedles.

The mold comprising both the first and second mixtures was then dried overnight in a sterile environment at room temperature, thereby forming the microneedle patch comprising the agent disposed on the periphery, and preferably an entire periphery, of each microneedle. The microneedle patch formed via this second method results in rapid release of the agent upon contact with the skin unlike microneedle patches formed via the first method, which exhibit slow and sustained release of the agent. Moreover, the microneedle patch formed via this second method comprise microneedles having a solid mechanical strength for the agent to be tested. An example of a microneedle patch formed via this second method may be found, e.g., in FIGS. 4B and 4D.

Example 3: Method of Making a Microneedle Patch Comprising a Plurality of Microneedles, Each Microneedle Comprising Layers of Alternately Higher and Lower Concentrations of an Agent A poly dimethyl siloxane (PDMS) mold, e.g., as shown in the embodiment of FIG. 6, was again utilized for microneedle preparation according to this third method. As noted above, The mold was previously etched with stainless steel microneedles fabricated by laser cutting techniques.

A first mixture of PVP, maltose, leucine, and dileucine was prepared as a slurry. The weight ratio of PVP to the combination of maltose, leucine, and dileucine was about 1:1 (PVP:maltose+leucine+dileucine=1:1). Approximately 30 µl of the first mixture was applied to the PDMS mold to form a first layer, and allowed to dry overnight.

Approximately 10 µl of the agent to be tested was then added to the mold comprising the dried first mixture. The newly added agent was allowed to dry over night at room temperature, thereby forming a second layer.

A second mixture of PVP, maltose, leucine, and dileucine was prepared as a slurry. Each of the maltose, leucine, and dileucine were mixed with the PVP in about a 1:1 weight ratio. Approximately 120 μl of the second mixture was applied to PDMS mold comprising the first and second layers.

The resulting mold was then dried, thereby forming multilayered microneedles having an layer comprising an agent located between two layers of composite material which do not comprise said agent. The microneedle patch formed via this fourth method results resulting in a sustained release of the agent.

Example 4: Method of Using a Microneedle Path in a Mouse Model

To evaluate a microneedle patch, as disclosed herein, the microneedle patch was stained with a blue dye, inserted into a 20 to 25% gelatin gel (w/v) for about 30 to 60 seconds, and removed to check the dissolution of the microneedles and release of the agent therefrom.

The long-term agent retaining abilities of the microneedle patch were tested using in vitro release studies. The microneedle patch was briefly immersed into about 200 μl of physiological saline for about 30 minutes, and the released agent was quantified by analytical methods. The agent of choice to establish the agent retaining ability of the microneedle patch was insulin, the release of which could be easily quantified by ELISA (enzyme-linked immunosorbent assay).

Figure 7A:
FIGS. 7A-7D depicts use of a microneedle patch in a mouse model, according to one embodiment.
Figure 7B:
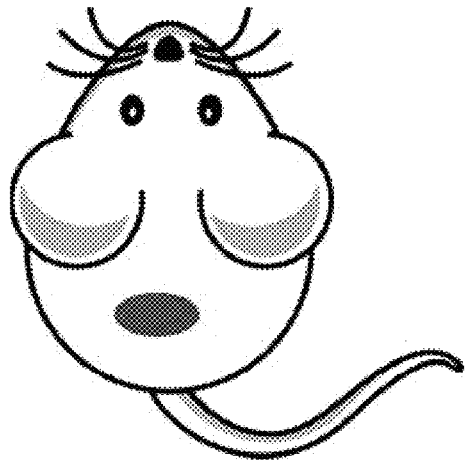
Figure 7C:
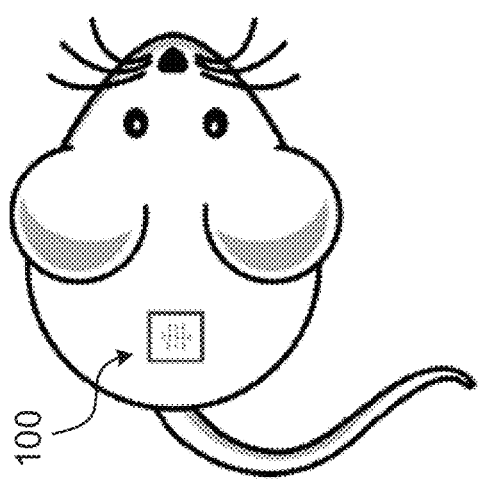
Figure 7D:
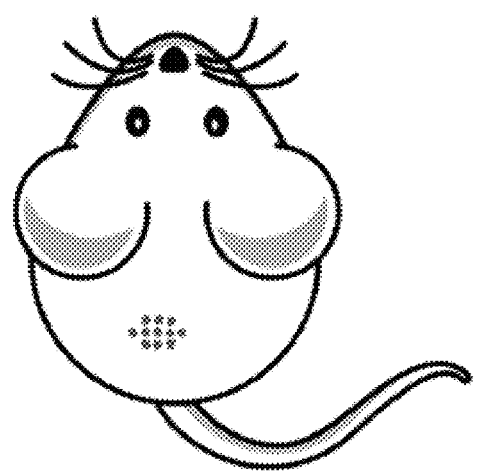

The in vivo agent release in an animal model was studied using mice. Briefly, the mice were anesthetized using isoflurane, and their backs shaved with clippers to remove the hair. The implant site was cleaned with povidone iodine solution to clear off the remaining hair and other debris. As shown in FIG. 7A, the microneedle patch 100 comprising the microneedles and agent associated therewith was inserted into the skin of the mice under anesthesia, and the responsiveness of the skin to the agent delivered upon dissolution of the microneedles was evaluated/captured at different time periods (see, e.g., FIGS. 7B-7D) using an infrared thermal camera 702.

The foregoing description of the present invention has been provided for the purposes of illustration and description. It is not intended to be exhaustive or to limit the invention to the precise forms disclosed. The breadth and scope of the present invention should not be limited by any of the above-described exemplary embodiments. Many modifications and variations will be apparent to the practitioner skilled in the art. The modifications and variations include any relevant combination of the disclosed features. The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. A microneedle patch for agent application on skin, comprising:
   a patch scaffold having a surface; and
   a plurality of microneedles disposed on the surface, wherein:
      each microneedle of the plurality of microneedles is capable of piercing the skin and comprises a plurality of layers coated on the entire exterior of each microneedle;
      each layer of the plurality of layers comprises a composite material comprising polyvinylpyrrolidone (PVP), maltose, leucine, and dileucine;
      at least two layers of the plurality of layers comprise different concentrations of an agent;
      the plurality of microneedles are disposed as discrete areas of equal dimensions on the surface; and
      microneedles in a first discrete area comprise an agent that is different from microneedles in a second discrete area.

2. The patch of claim 1, wherein each microneedle of the plurality of microneedles is configured to dissolve and thereby deliver the agent through the skin upon application.

3. The patch of claim 1, further comprising a pedestal on the surface for adhesion to the skin.

4. The patch of claim 1, wherein the composite material comprises about 70-90 wt. % PVP.

5. The patch of claim 1, wherein the agent is uniformly disposed within the composite material.

6. The patch of claim 1, wherein each microneedle of the plurality of microneedles comprises a tip portion proximate to a tip of the microneedle and a stem portion that is further distal from the tip.

7. The patch of claim 6, wherein the agent is not present in the stem portion, or is present at the stem portion at a lower concentration than in the tip portion.

8. The patch of claim 7, wherein the composite material is present at the tip portion at a lower concentration than in the stem portion.

9. The patch of claim 1, wherein the plurality of layers comprise alternately higher and lower concentrations of the agent.

10. The patch of claim 1, wherein the agent is coated on at least a portion of an outer surface of the composite material.

11. The patch of claim 1, wherein each microneedle of the plurality of microneedles comprises a substantially pyramidal shape.

12. The patch of claim 1, wherein the agent is a cosmetic or pharmaceutical preparation.

13. The patch of claim 12, wherein the patch is provided as a facial mask or a portion of a facial mask.

14. The patch of claim 1, further comprising an image sensor or a thermal sensor coupled to the patch scaffold and proximate each microneedle of the plurality of microneedles.

15. The patch of claim 1, wherein each layer of the plurality of layers has boundaries parallel to the periphery of each microneedle.

16. The patch of claim 1, wherein outer layers of the plurality of layers each comprise a conical shell and an innermost layer farthest from a tip portion of the microneedle comprises a conical layer.

17. The patch of claim 16, wherein a first layer nearest the tip portion comprises a concentration of the agent, a second layer farther from the tip portion than the first layer is devoid of the agent, and a third layer farther from the tip portion than the second layer comprises a second concentration of the agent, the concentration and the second concentration being greater than zero.

18. A method for determining an immune response in a mammal skin, the method comprising: applying the microneedle patch of claim 2 on the skin; and determining, via at least one sensor operatively coupled to the microneedle patch, whether the agent delivered to the mammal from each of the microneedles induces an immune response in the skin thereof.

19. The method of claim 18, wherein the at least one sensor comprises an image sensor or a thermal sensor.

20. A method for delivering a cosmetic or pharmaceutical agent to a mammal skin, the method comprising: applying the microneedle patch of claim 12 on the skin and allowing the cosmetic or pharmaceutical agent to be delivered to the skin.

* * * * *